(12) United States Patent
Souza et al.

(10) Patent No.: US 6,870,486 B2
(45) Date of Patent: Mar. 22, 2005

(54) SYSTEM AND METHOD FOR UTILIZING A PASTEURIZATION SENSOR

(75) Inventors: Leonardo de Oliveira de Freitas Souza, Sertãozinho (BR); Gilmar de Matos Caldeira, Ribeirão Preto (BR); Evaristo Orellana Alves, Sertãozinho (BR); Gilberto Selegatto, Serrana (BR)

(73) Assignee: Smar Research Corporation, Holbrook, NY (US)

(*) Notice: Subject to any disclaimer, the term of this patent is extended or adjusted under 35 U.S.C. 154(b) by 144 days.

(21) Appl. No.: 10/266,016

(22) Filed: Oct. 7, 2002

(65) Prior Publication Data

US 2004/0066314 A1 Apr. 8, 2004

(51) Int. Cl.[7] ............................................. G08B 21/00
(52) U.S. Cl. ................................... 340/870.16; 426/34
(58) Field of Search ....................... 340/870.16; 426/34; 99/453, 470

(56) References Cited

U.S. PATENT DOCUMENTS

| | | | |
|---|---|---|---|
| 4,161,909 A | * | 7/1979 | Wakeman ................ 99/453 |
| 4,576,781 A | | 3/1986 | Duncombe et al. |
| 5,022,013 A | * | 6/1991 | Dalton et al. .................. 367/4 |
| 5,106,202 A | | 4/1992 | Anderson et al. |
| 5,255,977 A | | 10/1993 | Eimer et al. |
| 5,871,308 A | * | 2/1999 | Valerino et al. ............ 406/186 |
| 5,882,244 A | | 3/1999 | Hiyama et al. |
| 6,208,253 B1 | | 3/2001 | Fletcher et al. |
| 6,369,894 B1 | | 4/2002 | Rasimas et al. |
| 2002/0024450 A1 | * | 2/2002 | Townsend et al. ..... 340/870.16 |

FOREIGN PATENT DOCUMENTS

WO    WO 02/27276 A1    4/2002

* cited by examiner

*Primary Examiner*—Timothy Edwards
(74) *Attorney, Agent, or Firm*—Dorsey & Whitney LLP

(57) ABSTRACT

An environmental condition sensing device arrangement and method for sensing an environmental condition are provided. A device case which is water-tight and/or air-tight is provided for sensing such condition. In addition, a sensing device configured to sense an environmental condition, a transmitter being operatively connected to the sensing device, and a power source supplying power to the sensing device and the transmitter are also provided. The sensing device, the transmitter and the power source are disposed within the device case.

51 Claims, 3 Drawing Sheets

SYSTEM AND METHOD FOR UTILIZING A PASTEURIZATION SENSOR

FIELD OF THE INVENTION

The present invention relates generally to a system and method for measuring an environmental condition, and more particularly to a system and method for measuring the environmental condition inside a sealed container during a pasteurization process and transmitting that measured environmental condition.

BACKGROUND OF THE INVENTION

Pasteurization involves an application of mild heat for a specified time to a liquid food or beverage to enhance its keeping properties, and to destroy any harmful microorganisms present. For milk, the times and temperatures employed for such pasteurization are based upon the thermal tolerance of *Mycobacterium tuberculosis*, one of the most heat resistant of non-spore-forming pathogens. Vegetative cells of most bacteria are generally eliminated by heat treatment, while endospores are unaffected.

In the food preparation industry, pasteurization is accomplished by placing a batch of liquid food or beverage containers (which generally includes several sealed bottles) into an oven or heated area at a particular temperature for a particular period of time based on the characteristics of the liquid food or beverage. By heating the liquid food or beverage, its keeping properties are enhanced, and harmful microorganisms are destroyed therein. Once the batch of liquid food or beverage is removed from the oven or heated area, a bottle of the liquid food or beverage is tested to determine if it has been properly pasteurized. Many times, the liquid inside the test bottle is properly pasteurized. At times, however, the liquid inside the test bottle may be overly pasteurized causing the liquid to be burnt or under pasteurized. Thus, the keeping properties may be underdeveloped, and/or harmful microorganisms are possibly allowed to survive. Over-pasteurization or under-pasteurization can be the product of inadequate modeling of the thermodynamic properties of the liquid food or beverage, unexpected or uneven heating of the oven or heating area, unexpected environmental conditions, variations in the temperature of the liquid food or beverage prior to the pasteurization process, or other manufacturing variants. If the liquid food or beverage inside the test bottle is over pasteurized or under pasteurized, the entire batch of liquid food or beverage must be destroyed.

Certain publications relate to systems and methods for measuring an environmental condition. For example, the U.S. Pat. No. 4,576,781 issued to Duncombe et al. describes a method for detecting a threshold temperature by providing a sensor which includes a magnet inside a ferromagnetic shield that has a lower Curie point than that of the magnet. Below the threshold temperature, the sensor is magnetically characterless. Above the threshold is reached, the sensor displays a magnetic character which is detected at a solid state magnetometer. The sensor can be located inside a sealed containment vessel, and the solid state magnetometer can be located outside the vessel.

U.S. Pat. No. 5,255,977 issued to Eimer et al. (the Eimer Patent) describes a method and apparatus for monitoring the heat transfer and therefore the efficiency of a condenser. A temperature probe is used to measure the temperature within an outlet chamber, and transmit the measured temperature to evaluating means. The temperature probe and the evaluating means are connected by lines. The Eimer Patent also discloses that it is possible to provide wireless transmission from the temperature probe to the evaluating means.

U.S. Pat. No. 6,208,253 issued to Fletcher et al. describes an apparatus and method for temperature sensing through observable, temperature dependent effects on an interrogating magnetic field facilitated by a sensing module. The sensing module has a signal element that interacts with the interrogation field to product a remotely readable magnetic response, and disposed proximate to the signal element. In a three-layer sensor implementation, a signal layer, a modulation layer and a bias layer are provided. The shunting effect of the modulation layer on the bias layer generally occurs more gradually than the demagnetization of the bias layer alone in a two-layer implementation. It is possible to fabricate a three-layer sensor that is operative over varying temperature ranges through a selection of modulation layer compositions having appropriate Curie temperatures. Additionally, the three-layer implementation has a reversible harmonic type, such that the three-layer temperature sensor continues to function even after the temperature of the modulation layer of the sensor falls below the Curie temperature of the modulation layer of the sensor, i.e., after the temperature has been above the Curie temperature for a period of time.

U.S. Pat. No. 6,369,894 issued to Rasimas et al. describes a modular fluorometer and a method of using the same to control an industrial water system. The modular fluorometer can be used with water from any water system, including with water used in industrial water systems (e.g., indirect contact cooling and heating water, such as pasteurization water). The modular fluorometer may accommodate a temperature sensor. Also, it is possible to use a wireless communication protocol between the modular fluorometer and a controller.

International Publication Number WO 02/27276 by Tietsworth et al. describes a flow meter and method for determining the corrected flow rate of a liquid falling into a predetermined class of liquids based on its viscosity and density. The flow meter includes a temperature sensor, which measures the temperature of the syrup and sends the measured temperature to a microprocessor. The flow meter can also include a wireless communication system.

However, none of the above publications describe a system and method which effectively and continuously monitors environmental conditions.

OBJECTS AND SUMMARY OF THE INVENTION

An object of the present invention is to provide an environmental condition sensing device which is operated continuously and effectively. The exemplary environmental sensing device configured to sense an environmental condition and including a device case which is water-tight and/or air-tight, a transmitter operatively connected to the sensing device, and a power source supplying power to the sensing device and the transmitter. According to an exemplary embodiment of the present invention, the sensing device, the transmitter and the power source are disposed within the device case.

In the exemplary method of sensing the environmental conditions, the power is provided by a power device to the sensing device and the transmitter that are disposed within the water-tight, air-tight case, the environmental conditions are sensed from within the case, and the sensed environmental conditions are transmitted from within the case. The sensing device can sense the environmental condition (e.g., temperature or pressure) in real time. In addition, the case can be situated within a sealed container which has a liquid, and the sensed environmental condition may be associated with a characteristic of the liquid inside the sealed container during a heating process, a cooling process and/or a pasteurization process. For example, the transmitter may receive a measurement of the environmental condition from the sensing device, and then transmit a signal indicative of the sensed environmental condition via wireless communication, e.g., over a non-predetermined distance, and/or via wired communication. A microprocessor can receive and evaluates the signal transmitted by the transmitter, and may calculate the pasteurization unit and bacteria level of the liquid based on the sensed environmental condition.

Still another object of the present invention is to provide an environmental condition sensing device which is configured to be placed within a sealed container containing a liquid during a pasteurization process. The sensing device includes a device case which is water-tight and/or air-tight, and configured to be placed within a sealed container containing a liquid during a pasteurization process.

Yet another object of the present invention is to provide a method for sensing environmental conditions within a sealed container containing a liquid during a pasteurization process. The method including steps of sensing an environmental condition of a liquid contained within a sealed container during a pasteurization process from within the case which is watertight and/or air-tight, and transmitting the sensed environmental condition from within the case.

BRIEF DESCRIPTION OF THE DRAWINGS

Further objects, features and advantages of the invention will become apparent from the following detailed description taken in conjunction with the accompanying figures showing illustrative embodiments of the invention, in which.

Figure 1A:
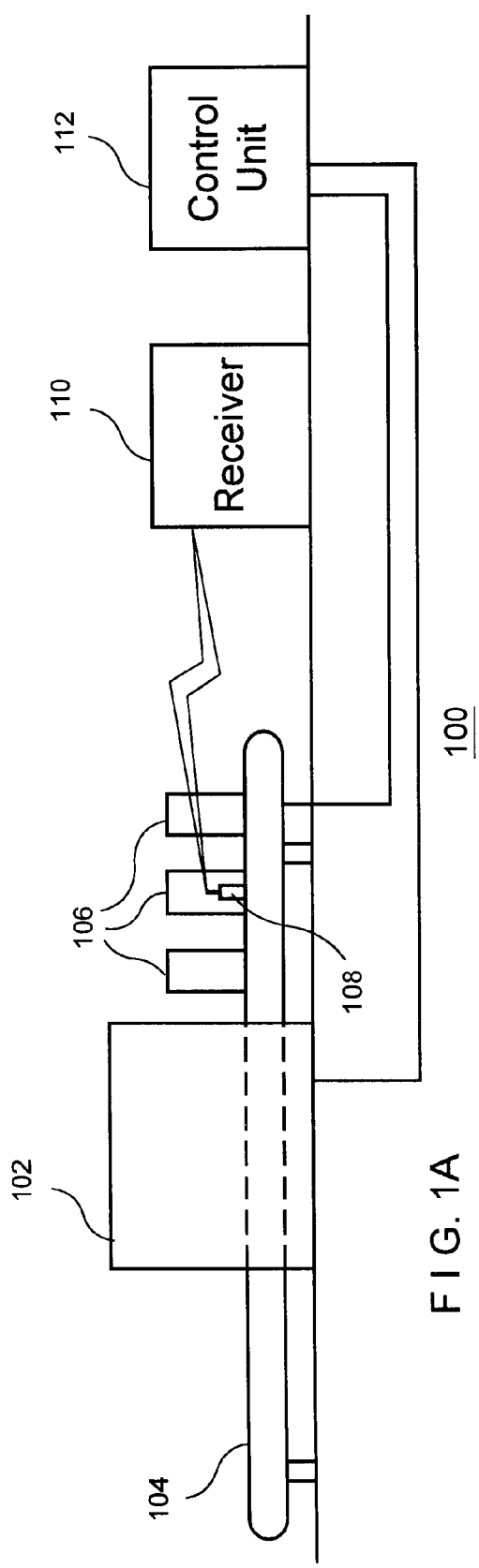
FIG. 1(a) is a block diagram of a process line that performs a pasteurization process on a batch of liquid food or beverage utilizing a wireless environmental condition sensing device, prior to heat being applied to a batch of liquid food or beverage according to a first exemplary embodiment of the present invention.

Throughout the figures, the same reference numerals and characters, unless otherwise stated, are used to denote like features, elements, components or portions of the illustrated embodiments. Moreover, while the present invention will now be described in detail with reference to the figures, it is done so in connection with the illustrative embodiments.

DETAILED DESCRIPTION OF PREFERRED EMBODIMENTS

FIG. 1(a) illustrates a first exemplary embodiment of a process line 100 according to the present invention that monitors environmental conditions during a pasteurization process prior to the beginning of this process, during the process and thereafter. The process line 100 includes a heating chamber 102, a conveyor mechanism 104, a receiver 110 and a control unit 112. The conveyor mechanism 104 passes through the heating chamber 102, such that objects placed on the conveyor mechanism 104 can be exposed to heat produced within the heating chamber 102 for a period of time, e.g. to effectuate the pasterization process.

During a pasteurization process, one or more containers 106 are placed on the conveyor mechanism 104 outside of the heating chamber 102. The containers 106 are typically sealed, and contain a liquid food or beverage. At least one of the containers 106 contains an environmental condition sensing device 108. The environmental condition sensing device 108 measures an environmental condition of the liquid within the one of the containers 106 (e.g., temperature or pressure), and transmits the measurement to the receiver 110 wirelessly.

In an exemplary embodiment, more than one of the containers 106 contain the environmental condition sensing device 108. In yet another embodiment, each of the containers 106 contains the environmental condition sensing device 108.

The exemplary environmental condition sensing device 108 illustrated in FIG. 1(a) transmits the measurements of the environmental condition to the receiver 110 utilizing a wireless transmitter via a wireless transmission protocol, such as Bluetooth. The transmission of measurements from the environmental condition sensing device 108 to the receiver 110. The receiver 110, in turn, transmits the measurements received from the environmental condition sensing device 108 to the control unit 112. The control unit 112 controls the heating chamber 102 and the conveyor mechanism 104.

Figure 1B:
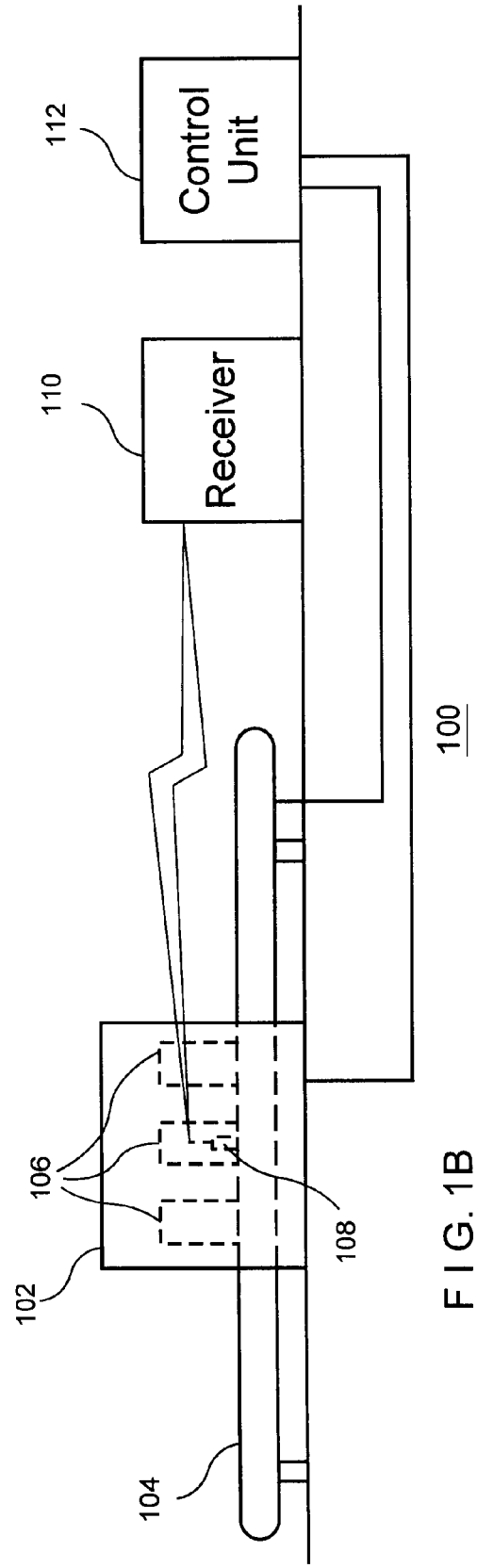
FIG. 1(b) is a block diagram of a process line of FIG. 1(c) while heat is being applied to the batch of liquid food or beverage.

Referring now to FIG. 1(b), which shows the process line 100 that is substantially the same as that of FIG. 1(a) except for the location of the containers 106 and the environmental condition sensing device 108, the pasteurization process begins when the control unit 112 causes the conveyor mechanism 104 to move the containers 106 into the heating chamber 102. The heating chamber 102 is controlled by the control unit 112, and is preheated to a predetermined temperature. The environmental condition sensing device 108 transmits measurements of the environmental condition to the receiver 110. The environmental condition measured by the environmental condition sensing device 108 is preferably the temperature of a fluid in the container 106 or an external temperature. The receiver 110 transmits these measurements to the control unit 112 utilizing a wireless device or a wired device. The control unit 112 utilizes this received information to compute the number of pasteurization units of the liquid in the containers 106. Once the liquid in the containers 106 reaches a predetermined number of pasteurization units, the liquid in the containers 104 is fully pasteurized, and the control unit 112 causes the conveyor mechanism 104 to move the containers 106 out from the heating chamber 102. In another exemplary embodiment, the environmental condition can be pressure, or the like.

Figure 1C:
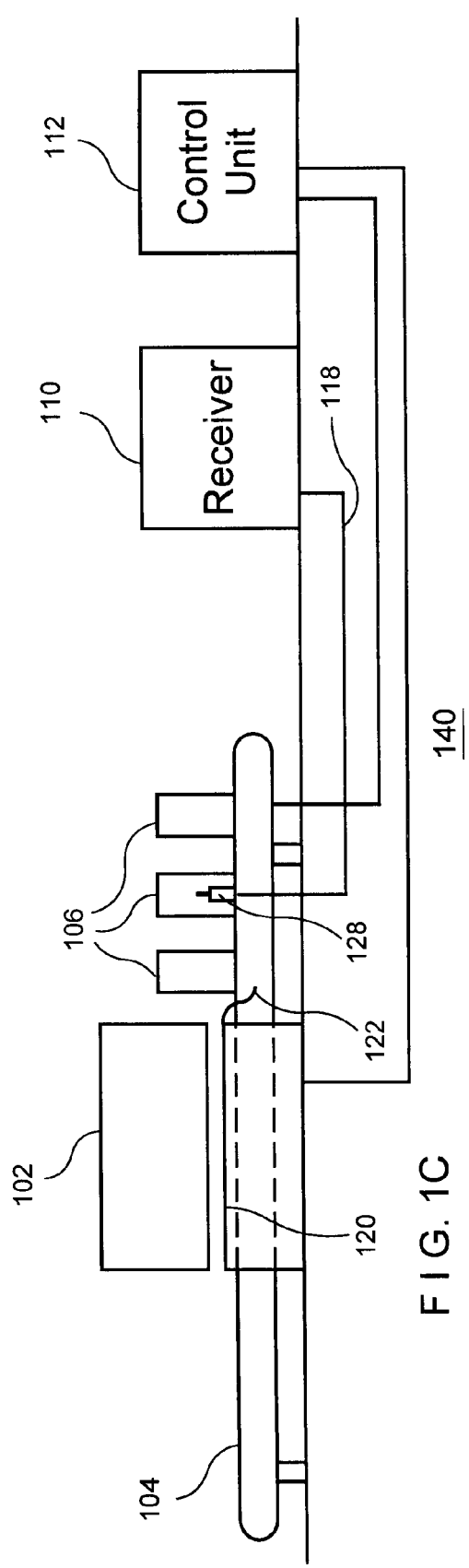
FIG. 1(c) is a block diagram of a process line that performs a pasteurization process on the batch of liquid food or beverage utilizing a wired environmental condition sensing device, prior to heat being applied to the batch of liquid food or beverage according to a second exemplary embodiment of the present invention.

FIG. 1(c) shows a second exemplary embodiment of a process line 140 according to the present invention, which is substantially similar to the process line 100 of FIGS. 1(a) and 1(b) except that the environmental condition sensor 108 is replaced by a wired environmental condition sensor 128, and a wire 118, a wire channel 120 and wire guide 122 are additionally provided. This process line 140 shown in FIG. 1(c) is illustrated for a time prior to the beginning of the pasteurization process. The process line 140, similarly to the process line 100, includes the heating chamber 102, the conveyor mechanism 104, the receiver 110 and the control unit 112. The conveyor mechanism 104 passes through the heating chamber 102, such that objects placed on the conveyor mechanism 104 can be exposed to heat produced within the heating chamber 102 for a period of time. The heating chamber 102 also includes the wire channel 120 and the wire guide 122. The wire channel 120 accommodates the wire 118 as the wired environmental condition sensor 128 passes through the heating chamber 102. The wire 118 allows the wired environmental condition sensor 128 to communicate with the receiver 110 in a wired manner. The wire can be an electrical wire, coaxial wire, etc.

During the pasteurization process, the containers 106 provided on the process line 140 are placed on the conveyor mechanism 104 outside of the heating chamber 102. The containers 106 are typically sealed and contain a liquid food or beverage. One of the containers 106 contains the environmental condition sensing device 128 which is wired to the receiver 110. The wired environmental condition sensing device 128 measures the environmental condition of the liquid within the one of the containers 106, e.g. temperature, pressure, etc., and transmits this measurement to the receiver 110 via the wire 118. In another exemplary embodiment of the present invention, more than one of the containers 106 contain the wired environmental condition sensing device 128. In yet another exemplary embodiment, each of the containers 106 contain the wired environmental condition sensing device 128.

The wired environmental condition sensing device 128 transmits measurements of the environmental condition to the receiver 110. The receiver 110 in turn transmits the measurements received from the wired environmental condition sensing device 128 to the control unit 112. The control unit 112 controls the heating chamber 102 and the conveyor mechanism 104.

Figure 1D:
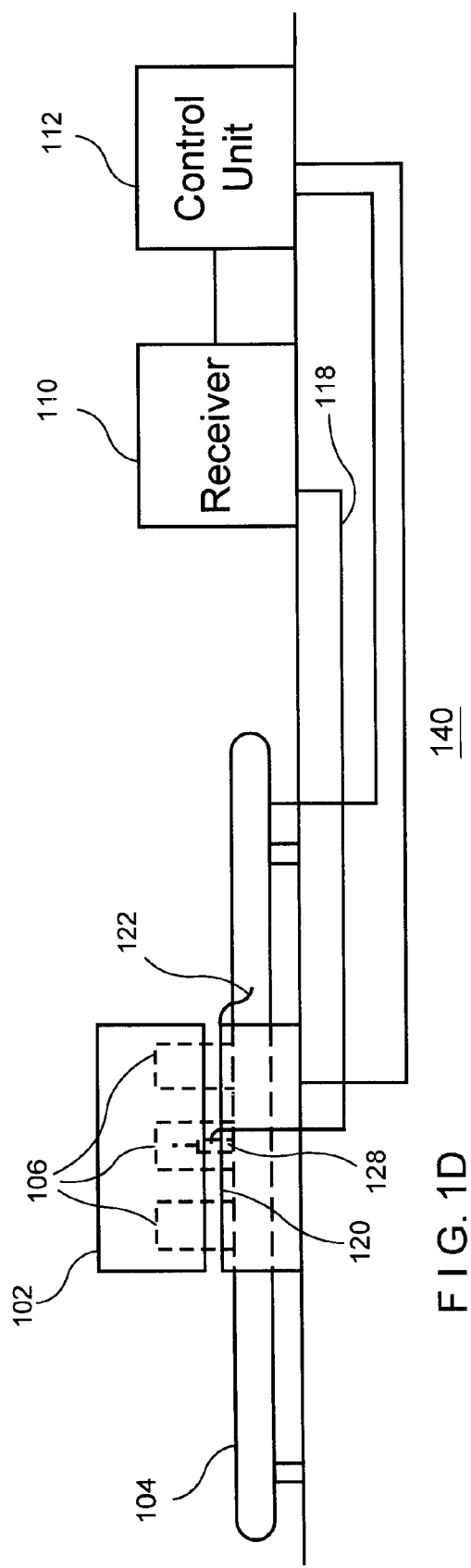
FIG. 1(d) is a block diagram of the process line of FIG. 1(c) that performs a pasteurization process while heat is being applied to the batch.

Referring now to FIG. 1(d), which shows the process line 140 that is substantially the same as that of FIG. 1(c) except for the location of the containers 106 and the wired environmental condition sensing device 128. The pasteurization process begins when the control unit 112 causes the conveyor mechanism 104 to move the containers 106 into the heating chamber 102. The heating chamber 102 is controlled by the control unit 112, and is preheated to a particular temperature. The wired environmental condition sensing device 128 transmits measurements of the environmental condition to the receiver 110. The environmental condition measured by the wired environmental condition sensing device 128 can be an internal or external temperature. The receiver 110 transmits these measurements to the control unit 112 via a wired or wireless manner. The control unit 112 utilizes this information to compute the number of pasteurization units of the liquid in the containers 106 as discussed above. Once the liquid in the containers 106 reaches a predetermined number of pasteurization units, the liquid in the containers 104 is fully pasteurized and the control unit 112 causes the conveyor mechanism 104 to move the containers 106 out of the heating chamber 102. In another exemplary embodiment of the present invention, the environmental condition is pressure, or the like. In yet another exemplary embodiment, the wire 118 can be replaced by a general purpose communication network. In still another exemplary embodiment, the wire 118 can be replaced by the connection to the Internet.

Figure 2:
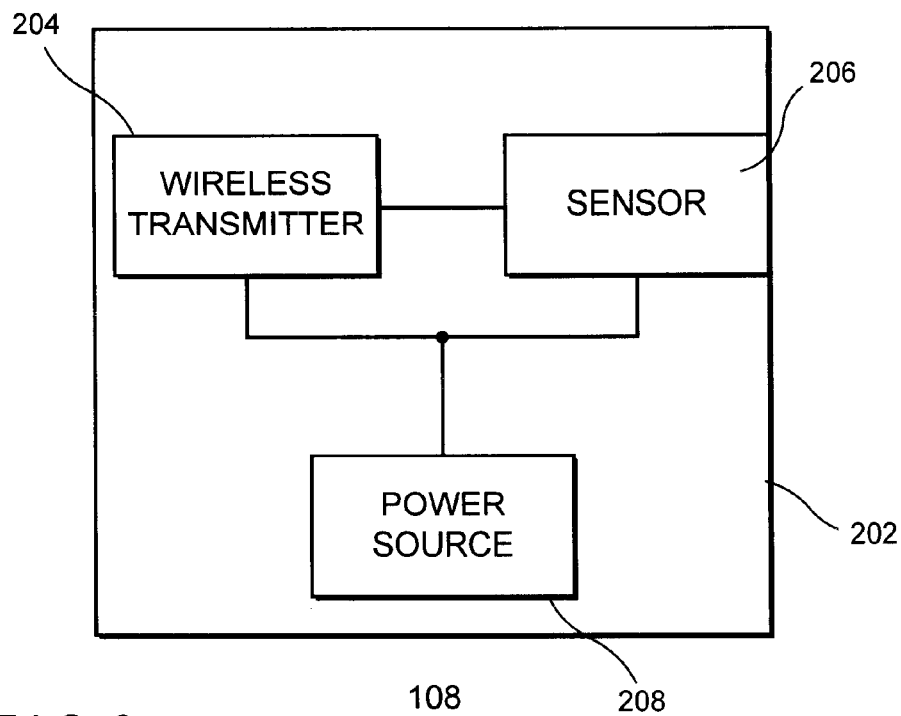
FIG. 2 is a block diagram of a first exemplary embodiment of an environmental condition sensing device according to the present invention.

FIG. 2 illustrates an exemplary embodiment of the environmental condition sensing device 108 of the first exemplary process line 100 shown in FIG. 1(a). The environmental condition sensing device 108 includes a case 202, a transmitter 204, a sensor 206 and a power source 208. The transmitter 204, the sensor 206 and the power source 208 are disposed within the case 202. The case 202 can preferably be water-tight and/or air-tight. The exemplary details of the environmental condition sensing device 108 is configured to transmit analog and/or digital signals indicative of an environmental condition of a substance or area measured by the sensor 206. The sensor 206 measures the environmental condition of the substance in real time over a range of values. The substance is located outside the case 202. The sensor 206 is in communication with the transmitter 204. The sensor 206 and the transmitter 204 are both connected to and powered by the power source 208 (e.g., a battery). The sensor 206 transmits the measurements of the environmental condition to the transmitter 204, and in turn, the transmitter 204 wirelessly transmits the received readings to the receiver 110. The transmitter 204 and the receiver 110 can be provided at a variable distance from one another, depending on the power of the transmitter 204. In another exemplary embodiment, the power source 208 is absent, and the transmitter 204 and the sensor 206 are powered by a remote power device (not shown).

Figure 3:
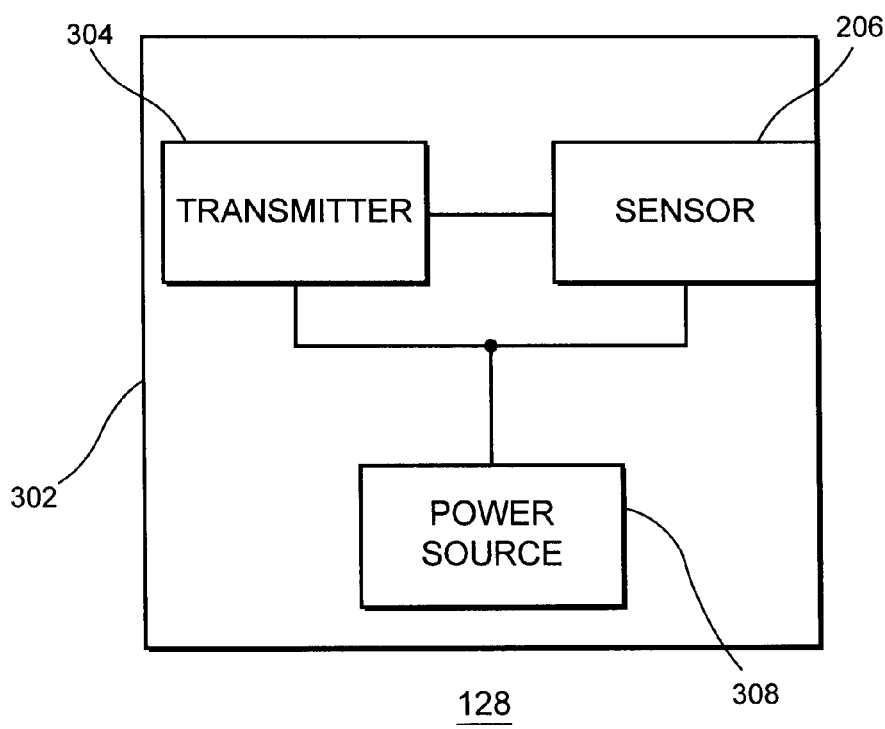
FIG. 3 is a block diagram of a second exemplary embodiment of the environmental condition sensing device according to the present invention.

FIG. 3 illustrates the exemplary details of the wired environmental condition sensing device 128 shown in FIG. 1(c). This environmental condition sensing device 128 also includes a case 302, a transmitter 304, a sensor 306 and a power source 308. The transmitter 304, the sensor 306 and the power source 308 are disposed within the case 302. The case 302 is water-tight and/or air-tight. The environmental condition sensing device 128 is configured to transmit digital signals indicative of an environmental condition of a substance measured by the sensor 306 via a wire. The sensor 306 measures the environmental-condition of the substance or area in real time over a range of values. The substance areas are preferably located outside the case 302. The sensor 306 is in communication with the transmitter 304, which are both connected to and powered by the power source 308 (e.g., a battery). The sensor 306 transmits readings of the environmental condition to the transmitter 304, and in turn, the transmitter 304 transmits the received readings to a receiver, here the receiver 110, utilizing a wired transmission protocol over a communication link (e.g., the wire 118). The transmitter 304 and the receiver 110 can be provided at a variable distance from one another, depending on the power of the transmitter 304 and possibly the length of the wire 118.

In another embodiment, the wire 118 can be replaced by a general purpose communication network or a connection to the Internet. In yet another exemplary embodiment of the present invention, the power source 308 is absent from the sensing device 128, and the transmitter 304 and the sensor 306 are powered by remote power devices. In yet another exemplary embodiment, the sensor 306 communicates with the receiver 110 directly via wired transmission.

While the invention has been described in connecting with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

What is claimed:

1. An environmental condition sensing arrangement comprising:
    a case being one of water-tight and air-tight;
    a sensing device configured to sense an environmental condition;
    a transmitter being operatively connected to the sensing device; and
    a power source supplying power to the sensing device and the transmitter, wherein the sensing device, the transmitter and the power source are disposed within the device case, wherein the case is situated within a sealed container which has a liquid, and wherein the sensed environmental condition is associated with a characteristic of the liquid inside the sealed container during at least one of a heating process and a cooling process.

2. The environmental condition sensing arrangement of claim 1, wherein the sensing device senses the environmental condition in real time.

3. The environmental condition sensing arrangement of claim 1, wherein the sensed environmental condition is temperature.

4. The environmental condition sensing arrangement of claim 1, wherein the sensed environmental condition is pressure.

5. An environmental condition sensing arrangement comprising:
    a case being one of water-tight and air-tight;
    a sensing device configured to sense an environmental condition;
    a transmitter being operatively connected to the sensing device; and
    a power source supplying power to the sensing device and the transmitter, wherein the sensing device, the transmitter and the power source are disposed within the device case, wherein the case is situated within a sealed container which has a liquid, and wherein the sensed environmental condition is associated with a characteristic of the liquid inside the sealed container during a pasteurization process.

6. The environmental condition sensing arrangement of claim 5, wherein the transmitter receives a measurement of the environmental condition from the sensing device.

7. The environmental condition sensing arrangement of claim 6, wherein the transmitter transmits a signal indicative of the sensed environmental condition via wired communication.

8. The environmental condition sensing arrangement of claim 6, wherein the transmitter transmits a signal indicative of the sensed environmental condition via wireless communication.

9. The environmental condition sensing arrangement of claim 8, wherein the signal is transmitted over a non-predetermined distance.

10. The environmental condition sensing arrangement of claim 6, further comprising a microprocessor which receives and evaluates the signal transmitted by the transmitter.

11. The environmental condition sensing arrangement of claim 10, wherein the microprocessor calculates the pasteurization unit and bacteria level of the liquid based on the sensed environmental condition.

12. The environmental condition sensing arrangement of claim 10, wherein the environmental condition is temperature of the liquid.

13. A method of sensing environmental conditions, comprising:
    providing power by a power device to a sensing device and a transmitter, the power device, the sensing device and the transmitter being disposed within a case which is one of water-tight and air-tight;
    sensing an environmental condition from within the case; and
    transmitting the sensed environmental condition from within the case, wherein the case is situated within a sealed container which has a liquid, and wherein the sensed environmental condition is associated with a characteristic of the liquid inside the sealed container during at least one of a heating process and a cooling process.

14. The method of claim 13, wherein the sensing device senses the environmental condition in real time.

15. The method of claim 13, wherein the environmental condition is temperature.

16. The method of claim 13, wherein the environmental condition is pressure.

17. A method of sensing environmental conditions, comprising:
    providing power by a power device to a sensing device and a transmitter, the power device, the sensing device and the transmitter being disposed within a case which is one of water-tight and air-tight;
    sensing an environmental condition from within the case; and
    transmitting the sensed environmental condition from within the case, wherein the case is situated within a sealed container which has a liquid, and wherein the sensed environmental condition is associated with a characteristic of the liquid inside the sealed container during a pasteurization process.

18. The method claim 17, wherein the transmitter receives a measurement of the environmental condition from the sensing device.

19. The method of claim 18, wherein the transmitter transmits a signal indicative of the sensed environmental condition via wired communication.

20. The method of claim 18, wherein the transmitter transmits a signal indicative of the sensed environmental condition via wireless communication.

21. The method of claim 20, wherein the signal is transmitted over a non-predetermined distance.

22. The method of claim 18, wherein a microprocessor receives the signal transmitted by the transmitter.

23. The method of claim 22, further comprising calculating with the microprocessor, the pasteurization unit and bacteria level of the liquid based on the sensed environmental condition.

24. The method of claim 22, wherein the environmental condition is temperature of the liquid.

25. An environmental condition sensing arrangement configured to be placed within a sealed container containing a liquid during a pasteurization process, comprising:
    a device case being one of water-tight and air-tight, wherein the device case is configured to be placed within a sealed container containing a liquid during a pasteurization process;

a sensing device configured to sense an environmental condition; and a transmitter being operatively connected to the sensing device, wherein the sensing device and the transmitter are disposed within the device case.

26. The environmental condition sensing arrangement of claim 25, wherein the sensing device senses the environmental condition in real time.

27. The environmental condition sensing device of claim 25, wherein the environmental condition is temperature.

28. The environmental condition sensing apparatus of claim 25, wherein the environmental condition is pressure.

29. The environmental condition sensing apparatus of claim 25, wherein the case is situated within a sealed container which has a liquid, and wherein the sensed environmental condition is associated with a characteristic of the liquid inside the sealed container during at least one of a heating process and the cooling process.

30. The environmental condition sensing apparatus of claim 25, wherein the case is situated within a sealed container which has a liquid, and wherein the sensed environmental condition is associated with a characteristic of the liquid inside the sealed container during the pasteurization process.

31. The environmental condition sensing apparatus of claim 30, wherein the transmitter receives a measurement of the environmental condition from the sensing device.

32. The environmental condition sensing apparatus of claim 31, wherein the transmitter transmits a signal indicative of the sensed environmental condition via wired communication.

33. The environmental condition sensing apparatus of claim 31, wherein the transmitter transmits a signal indicative of the sensed environmental condition via wireless communication.

34. The environmental condition sensing apparatus of claim 33, wherein the signal is transmitted over a non-predetermined distance.

35. The environmental condition sensing apparatus of claim 31, further comprising a microprocessor which receives and evaluates the signal transmitted by the transmitter.

36. The environmental condition sensing apparatus of claim 35, wherein the microprocessor calculates the pasteurization unit and bacteria level of the liquid based on the sensed environmental condition.

37. The environmental condition sensing apparatus of claim 35, wherein the environmental condition is temperature of the liquid.

38. A method of sensing environmental conditions of within a sealed container containing a liquid during a pasteurization process, comprising:

sensing an environmental condition of a liquid contained within a sealed container with a sensing device during a pasteurization process from within a case which is one of water-tight and air-tight; and transmitting the sensed environmental condition by a transmitter situated within the case.

39. The method of claim 38, wherein the sensing device senses the environmental condition in real time.

40. The method of claim 38, wherein the environmental condition is temperature.

41. The method of claim 38, wherein the environmental condition is pressure.

42. The method of claim 38, wherein the case is situated within a sealed container, which has a liquid, and wherein the sensed environmental condition is associated with a characteristic of the liquid inside the sealed container during at least one of a heating process and a cooling process.

43. The method of claim 38, wherein the case is situated within a sealed container, which has a liquid, and wherein the sensed environmental condition is associated with a characteristic of the liquid inside the sealed container during the pasteurization process.

44. The method of claim 43, wherein the transmitter receives a measurement of the environmental condition from the sensing device.

45. The method of claim 44, wherein the transmitter transmits a signal indicative of the sensed environmental condition via wireless communication.

46. The method of claim 45, wherein the signal is transmitted over a non-predetermined distance.

47. The method of claim 44, wherein the transmitter transmits a signal indicative of the sensed environmental condition via wired communication.

48. The method of sensing environmental conditions of claim 44, further comprising a microprocessor which receives and evaluates the signal transmitted by the transmitter.

49. The method of claim 48, wherein the microprocessor calculates the pasteurization unit and bacteria level of the liquid based on the sensed environmental condition.

50. The method of claim 48, wherein the environmental condition is temperature of the liquid.

51. An environmental condition sensing arrangement comprising:

a case being one of water-tight and air-tight and situated within a sealed container;

a sensing device configured to sense an environmental condition;

a transmitter being operatively connected to the sensing device; and a power source supplying power to the sensing device and the transmitter, wherein the sensing device, the transmitter and the power source are disposed within the device case.

* * * * *